US010169535B2

(12) United States Patent
 Mentis (10) Patent No.: US 10,169,535 B2
(45) Date of Patent: Jan. 1, 2019

(54) ANNOTATION OF ENDOSCOPIC VIDEO USING GESTURE AND VOICE COMMANDS

(71) Applicant: UNIVERSITY OF MARYLAND BALTMORE COUNTY, Baltimore, MD (US)

(72) Inventor: Helena Mentis, Baltimore, MD (US)

(73) Assignee: The University of Maryland, Baltimore County, Baltimore, MD (US)

( * ) Notice: Subject to any disclaimer, the term of this patent is extended or adjusted under 35 U.S.C. 154(b) by 272 days.

(21) Appl. No.: 15/001,218

(22) Filed: Jan. 19, 2016

(65) Prior Publication Data

US 2016/0210411 A1   Jul. 21, 2016

Related U.S. Application Data

(60) Provisional application No. 62/104,178, filed on Jan. 16, 2015, provisional application No. 62/270,167, filed on Dec. 21, 2015.

(51) Int. Cl.
| H04N 5/00 | (2011.01) |
| G06F 19/00 | (2018.01) |
| G06F 3/01 | (2006.01) |
| G06F 3/0484 | (2013.01) |
| G06F 3/0482 | (2013.01) |
| G11B 27/34 | (2006.01) |
| A61B 1/00 | (2006.01) |
| G06F 3/16 | (2006.01) |
| H04N 5/225 | (2006.01) |

(52) U.S. Cl.
CPC .......... *G06F 19/321* (2013.01); *A61B 1/0005* (2013.01); *A61B 1/00041* (2013.01); *G06F 3/017* (2013.01); *G06F 3/0482* (2013.01); *G06F 3/04842* (2013.01); *G11B 27/34* (2013.01); *G06F 3/167* (2013.01); *H04N 2005/2255* (2013.01)

(58) Field of Classification Search
CPC .. G02B 27/01; G02B 27/017; G02B 27/0093; G02B 2027/014; A61B 5/1114; A61B 90/37; A61B 5/7445; A61B 5/742; A61B 5/4848; A61B 5/6803; A61B 2090/372
See application file for complete search history.

(56) References Cited

U.S. PATENT DOCUMENTS

| 5,262,871 | A | * | 11/1993 | Wilder | H01L 27/14609 257/E27.132 |
| 5,859,921 | A | * | 1/1999 | Suzuki | G06K 9/00268 382/118 |
| 6,198,485 | B1 | * | 3/2001 | Mack | G06F 3/013 345/419 |
| 6,486,799 | B1 | * | 11/2002 | Still | G01C 23/005 340/961 |
| 7,492,926 | B2 | * | 2/2009 | Kang | G06K 9/00604 382/117 |
| 7,697,024 | B2 | * | 4/2010 | Currivan | H04N 7/141 348/14.01 |
| 7,894,666 | B2 | * | 2/2011 | Mitarai | G06K 9/0061 382/167 |

(Continued)

*Primary Examiner* — Frank F Huang
(74) *Attorney, Agent, or Firm* — Juneau & Mitchell; Todd L. Juneau (57) ABSTRACT

The invention relates to annotating live video during endoscopy medical procedures.

19 Claims, 4 Drawing Sheets

(56) References Cited

U.S. PATENT DOCUMENTS

| | | | | |
|---|---|---|---|---|
| 8,159,519 B2* | 4/2012 | Kurtz | ............... | H04N 7/147 |
| | | | | 348/14.01 |
| 8,305,899 B2* | 11/2012 | Luo | ............ | H04L 47/10 |
| | | | | 370/236 |
| 8,432,492 B2* | 4/2013 | Deigmoeller | ...... | G06K 9/00624 |
| | | | | 348/581 |
| 9,438,819 B2* | 9/2016 | Van Broeck | ............ | G06F 3/013 |
| 9,727,790 B1* | 8/2017 | Vaziri | ............... | G06K 9/00771 |
| 2010/0053555 A1* | 3/2010 | Enriquez | ............... | A61B 3/113 |
| | | | | 351/210 |
| 2011/0279666 A1* | 11/2011 | Strombom | ............ | A61B 3/113 |
| | | | | 348/78 |
| 2014/0198190 A1* | 7/2014 | Okumu | ............... | G02B 27/017 |
| | | | | 348/53 |

* cited by examiner

ANNOTATION OF ENDOSCOPIC VIDEO USING GESTURE AND VOICE COMMANDS

CROSS REFERENCE TO RELATED APPLICATIONS

This application claims priority benefit under 35 USC 119(e) to U.S. provisional 62/104,178 filed Jan. 16, 2015, and to U.S. provisional 62/270,167, filed Dec. 21, 2015.

NAMES OF PARTIES TO A JOINT RESEARCH AGREEMENT

Not Applicable.

SEQUENCE LISTING

Not Applicable.

STATEMENT REGARDING FEDERALLY SPONSORED RESEARCH

The U.S. government has certain rights in this invention pursuant to NSF research grant number 1422671 and 1506889.

BACKGROUND OF THE INVENTION

1. Field of the Invention

The invention relates to annotating live video during endoscopy medical procedures.

2. Description of the Related Art

There is a substantial body of literature that addresses vision as situated and interactional. Specifically, studies of medical image use discuss the negotiations around and interpretation of images in clinical and surgical work and the ways these unfolding interventions manifest themselves as integral to medical decision-making. As Prasad showed in the seeing practices of the radiologist, cross-referencing of different images and diagnostic data constitute one's ability to detect and fix pathology. However, even in the radiology suite, cross-referencing through differential analysis is reliant on the diagrams and notations that are used to interpret MR images. Alac, in a study of neuroscientists' use of fMRI brain images, observed the gesturing and manipulation of digital displays during discussion in order to collaboratively understand and make meaningful what they were seeing.

Their gestural engagements are a phenomenal action to meld the digital, abstract images and the physical, concrete body through bodily orientation, gestures, and discussion. This can be seen in the way surgeons step through head or abdominal MR image slices as demonstrated by Johnson et al.'s discussion of interventional radiologists viewing the temporal sequencing of images when stepping through fluoroscopic X-ray images. It can also be seen in Lammer's rich detail on IR procedures where she articulates the eyes-on, hands-on tactility of the radiologist, whereby tactile resistances from wires and catheters are combined ("mutually interpenetrated") with x-ray image "roadmaps" to explore inside the body. These 'hands-on' interactions are significant in how imaging work practices are collaboratively organized.

In modern day surgical interventions, medical imaging has come to play an increasingly important role, particularly when enabling minimally invasive procedures. These are procedures that enter the body through small incisions or existing body cavities in order to minimize anatomical damage, reduce recovery time, and minimize the risk for infection. Traditionally, minimally invasive procedures are supported by intra-procedure imaging (e.g. endoscope, ultrasound), which provides real-time feedback. However, the practice of surgery is still reliant on the ability of the surgeons to resolve the body before them with the abstract representations of anatomy from books and diagrams. Hirschauer describes in his sociological account of the practices of surgery that dissection is a process through which the internal body is made visible and identifiable in relation to these abstract representations. This method of viewing the body is a part of the training and visual learning of human anatomy that a surgeon must undergo—to see the body as parts that are separable from the whole body. Evidence of this in surgery is also seen in how the body part that is of interest is delineated during surgery by removing all other parts from view through sterile coverings and drapes. But the body itself can also present facts in which the images must be resolved, as the process of uncovering, identifying, and resolving between the material body and the representation of the body is reflexive and iterative. As a result, surgery is a complex process of resolving the physical body as it lies before the surgeon with what one knows—both learned from experience and expected from preliminary work—and this does not occur only once or twice, but continually throughout a medical intervention.

What is important to note is that, in minimally invasive surgeries, the body is not available for exposition. In these cases, the focus of manipulating and annotating is on the supporting images, the outcome of which is the production of a docile object. Borrowed from Foucault's docile bodies and Garfinkel's docile record, Lynch refers to scientific images as docile objects when they have become observable, measurable, and quantifiable. In other words, the image is behaving in a manner that conforms to the needs of the surgeon. Simply producing and presenting an image does not directly translate to an effective medical gaze.

With the introduction of the Kinect sensor and API, there has been a surge of interest in providing sterile interaction with medical images during surgery through gesture and voice commands. The belief is that surgery time can be lessened by putting these high-fidelity images in the hands of the surgeon by the tableside during procedures, as opposed to being manipulated by a non-surgeon body. This rhetoric stems from concerns in the amount of time and room for error that arises when a third party, typically a support nurse who is not familiar with the anatomy, is asked to serve as the arms and hands of the surgical team.

There are a number of studies that discuss the negotiations around and interpretation of images in scientific and medical work and the ways these unfolding interventions manifest themselves as integral to decision-making. Oftentimes, these discussions involve gestures, deictic referencing, and manipulation of digital images. These 'hands-on' interactions are significant in how imaging work practices are organized.

Several authors have pointed out the issues that can arise. In one example, a surgeon instructed an assistant for seven minutes in order to click on an exact place on the interface with a mouse. While extreme, it illustrates the potential communication difficulties associated with image manipulation by proxy, in particular when the proxy does not share the same level of "professional vision". There is also a move towards further interaction at the bedside, primarily to afford surgeons the option to interact with the imaging systems while they are conducting the surgery itself.

BRIEF SUMMARY OF THE INVENTION

In a preferred embodiment, there is provided a method for annotating endoscopic video display during an endoscopic procedure implemented at least in part by a computer, the method comprising the steps of: (i) displaying a first user interface capable of providing a view of video from an endoscopic camera; (ii) displaying a second user interface associated with annotating the video, the second user interface overlaying the first user interface; (iii) receiving a voice command or gesture command to select an annotation tool associated with the second user interface; (iv) receiving an annotation to the video from the annotation tool, the annotation comprising a user image and a video position tag; and (v) displaying the annotation associated with the second user interface overlaid over the first user interface.

In another preferred aspect, the inventive method provides wherein the annotation comprises one or more graphical annotations.

In another preferred aspect, the inventive method provides wherein the video is recorded and stored with the annotation.

In another preferred aspect, the inventive method provides wherein the video is live video displayed concurrent with the output from the endoscopic camera, and the annotation is a persistent annotation.

In another preferred aspect, the inventive method provides wherein the step of receiving a voice command or gesture command is performed by two or more persons.

In another preferred aspect, the inventive method provides wherein the two or more persons are remote from each other and not at the same location.

In another preferred aspect, the inventive method provides wherein the step of receiving an annotation is performed by two or more annotation tools.

In another preferred aspect, the inventive method provides wherein the two or more annotation tools annotate in different colors.

In another preferred aspect, the inventive method provides wherein the two or more annotation tools are remote from each other and are not operated at the same location, and the output from the two or more annotation tools are each separately displayed to the same second user interface.

In a preferred embodiment, there is provided a system for annotating endoscopic video display during an endoscopic surgical procedure, comprising: (i) an endoscopy apparatus, the endoscopy apparatus comprising a an endoscope, the endoscope comprising a rigid or flexible tube, a light source directed via a fiber optic system into the tube, an imaging component disposed within the tube for transmitting image or video to a display screen, and one or more medical instruments disposed within the tube for performing a medical procedure; (ii) a computing system in operative association with the endoscopy apparatus, wherein the computer system is configured to receive, store, and process the transmitted image or video; (iii) one or more displays connected to the computing system, the one or more displays configured to receive and display the transmitted image or video; (iv) a gesture command input device connected to the computing system; (v) a voice command input device connected to the computing system; and, (vi) an annotation tool for pointing on or annotating the image or video, the annotation tool comprising program instructions stored on non-transitory computer-readable storage media that upon execution by a processor associated with the computing system receives input from the gesture command input device and the voice command input device and outputs one or more annotations to the one or more displays.

In a preferred aspect, the system provides two computer systems. The endoscope has its own computer and video is output to a secondary computer, where the video is then overlaid with the annotations, and then output again to the display. In this way, there is no need to configure a closed endoscopy computer and allows the use of a secondary computer that already has the correct (Kinect) drivers, video compression, input ports e.g. DVI, output ports and so forth. It is contemplated as within the scope of the invention, however, to put this system on a closed endoscopy computer.

In a preferred aspect, the system also provides wherein the computing system outputs a first user interface and a second user interface, the first user interface capable of providing a view of video from the endoscopy apparatus, the second user interface associated with annotating the video, the second user interface overlaying the first user interface, wherein in response to a voice command or gesture command, the annotation tool outputs an annotation to the video, the annotation comprising a user image and a video position tag, the annotation associated with the second user interface, and the second user interface is overlaid over the first user interface.

In a preferred aspect, the system also provides wherein the video is live video displayed concurrent with the output from the endoscopic camera, and the annotation is a persistent annotation.

In a preferred aspect, the system also provides wherein the system further comprises a second gesture command input device and a second voice command input device, capable of operation by a second person. In another preferred aspect, the same gesture and voice command device can be used by two people at the same time if they are collocated. For instance, a Kinect can pick up more than one person at the same time and each could have their own pointer.

In a preferred aspect, the system also provides wherein the second gesture command input device and the second voice command input device, capable of operation by a second person, are remote from the first gesture command input device and the first voice command input device, and not at the same location.

In a preferred aspect, the system also provides wherein the system further comprises a second annotation tool.

In a preferred aspect, the system also provides wherein the first and second annotation tools annotate in different colors.

In a preferred aspect, the system also provides wherein the first and second annotation tools are remote from each other and are not operated at the same location, and the output from the first and second annotation tools are each separately displayed to the same second user interface.

In another preferred embodiment, there is provided a graphical user interface, comprising: (i) a display portion that receives video output from an endoscopy apparatus; (ii) a display portion that provides a link to an image/video library; and (iii) a display portion that provides one or more control button links to a video annotation tool.

In another aspect, there is provided the graphical user interface, wherein the one or more button links further comprises a reference pointer, a reset, and an image or video capture.

BRIEF DESCRIPTION OF THE DRAWINGS

FIG. 4 also shows sample command dialogue boxes with the first and third dialogue box being annotation commands and the second dialogue box containing standard surgical communications which are filtered and not sent to the annotation system.

DETAILED DESCRIPTION OF THE INVENTION

The subject matter described herein includes the following basic components of the system for annotating endoscopic video display during an endoscopic surgical procedure: endoscopy machine, computing system, one or more displays, a Microsoft Kinect or similar gesture command input device, a microphone voice command input device, video display software, and annotation tool software.

Endoscopy Apparatus

The present invention contemplates various types of endoscopy devices as within the scope of the invention. An endoscope generally consists of a rigid or flexible tube, a light source directed via a fiber optic system into the tube, an optical lens for transmitting images, a camera for transmitting the images or video to a display screen, and one or more medical instruments disposed within the channel of the tube for performing medical procedures.

Endoscopes are used to gather information, obtain biopsies, and/or treat internal tissues and organs within a human or animal body. Tissues and organs may include the gastrointestinal tract, the respiratory tract, the urinary tract, reproductive systems, internal cavities from the abdominal region and pelvic region, pulmonary and cardiovascular systems (pleural, mediastinal, and extremity), joint, skull and bone regions, as well as ophthalmic and ENT systems.

Exemplary endoscopes may include devices made by Stryker, Cook Medical, Braun, Karl Storz, Misonix, Sumitomo, Ethicon, Viking, SIG, C. R. Bard, Smith & Nephew, Welch Allyn, ConMed, JMS, Fujifilm, and so forth. In a preferred aspect, the Stryker Park Trainer can provide a training system, but the Stryker Park Trainer also utilizes many of the same components that is in their standard endoscopic system used in surgery.

Computing System

The computer system is used to process the video annotations and to output the video feed and the annotations to the one or more display screens within the sterile surgical suite. The computer system is usually within the sterile area right next to the endoscopic computer, but it can be located outside of the sterile surgical suite.

Examples of well known computing systems, environments, and/or configurations that may be suitable for use with aspects of the subject matter described herein include, but are not limited to, personal computers, server computers, hand-held or laptop devices, multiprocessor systems, microcontroller-based systems, set top boxes, programmable consumer electronics, network PCs, minicomputers, mainframe computers, distributed computing environments that include any of the above systems or devices, and the like.

Aspects of the subject matter described herein may be described in the general context of computer-executable instructions, such as program modules, being executed by a computer. Generally, program modules include routines, programs, objects, components, data structures, and so forth, which perform particular tasks or implement particular abstract data types. Aspects of the subject matter described herein may also be practiced in distributed computing environments where tasks are performed by remote processing devices that are linked through a communications network. In a distributed computing environment, program modules may be located in both local and remote computer storage media including memory storage devices.

Components of the computer may include, but are not limited to, a processing unit, a system memory, and a system bus that couples various system components including the system memory to the processing unit. The system bus may be any of several types of bus structures including a memory bus or memory controller, a peripheral bus, and a local bus using any of a variety of bus architectures.

The computer system will typically include a variety of computer-readable media that can be accessed by the computer and includes both volatile and nonvolatile media, and removable and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile discs (DVDs) or other optical disk storage, magnetic cassettes, magnetic tape, magnetic disk storage or other magnetic storage devices, or any other medium which can be used to store the desired information and which can be accessed by the computer. Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The system memory includes computer storage media in the form of volatile and/or nonvolatile memory such as read only memory (ROM) and random access memory (RAM). A basic input/output system (BIOS), containing the basic routines that help to transfer information between elements within computer such as during start-up, is typically stored in ROM. RAM typically contains data and/or program modules that are immediately accessible to and/or presently being operated on by processing unit.

The computer may also include other removable/non-removable, volatile/nonvolatile computer storage media. By way of example only, a hard disk drive that reads from or writes to non-removable, nonvolatile magnetic media, a magnetic disk drive that reads from or writes to a removable, nonvolatile magnetic disk, and an optical disc drive that reads from or writes to a removable, nonvolatile optical disc such as a CD ROM or other optical media are contemplated. Other removable/non-removable, volatile/nonvolatile computer storage media that can be used in the exemplary operating environment include, but are not limited to, magnetic tape cassettes, flash memory cards, digital versatile discs, digital video tape, solid state RAM, solid state ROM, and the like. The hard disk drive is typically connected to the system bus through a non-removable memory interface such as interface and magnetic disk drive and optical disc drive are typically connected to the system bus by a removable memory interface.

The drives and their associated computer storage media, discussed above, provide storage of computer-readable instructions, data structures, program modules, and other data for the computer. A user may enter commands and information into the computer through input devices such as a keyboard and pointing device, commonly referred to as a mouse, trackball or touch pad. Other input devices (not shown) may include a microphone, joystick, game pad, satellite dish, scanner, a touch-sensitive screen of a handheld PC or other writing tablet, or the like. These and other input devices are often connected to the processing unit through a user input interface that is coupled to the system bus, but may be connected by other interface and bus structures, such as a parallel port, game port or a universal serial bus (USB). A monitor or other type of display device is also connected to the system bus via an interface, such as a video interface. In addition to the monitor, computers may also include other peripheral output devices, which may be connected through an output peripheral interface.

The computer may operate in a networked environment using logical connections to one or more remote computers, such as a remote computer. Logical connections may include a local area network (LAN) and a wide area network (WAN), but may also include other networks. Such networking environments are commonplace in offices, enterprise-wide computer networks, intranets and the Internet.

When used in a LAN networking environment, the computer is connected to the LAN through a network interface or adapter. When used in a WAN networking environment, the computer typically includes a modem or other means for establishing communications over the WAN, such as the Internet. It will be appreciated that the network connections shown are exemplary and other means of establishing a communications link between the computers may be used.

Displays

One or more displays may be used within the surgical suite where the endoscopy is being performed. If two or more display screens are used, it is contemplated that the same video feed can be played simultaneously on each screen. Alternatively, each screen can receive its own video feed, depending on the number of lenses/endoscopes broadcasting from the endoscopic procedure.

Gesture Command Input Device

In one embodiment, the gesture command (and voice command) input device is the Microsoft Kinect device. In another embodiment, the gesture input device is the Myo device, see e.g. https://www.myo.com/. In yet another embodiment, the gesture input device may be a LEAP motion device.

Kinect is a device that collects video and audio information from a room where it is located. The Kinect has a camera and a microphone array and specialized software that is able to detect, recognize, interpret and track human movements and facial gestures. The Kinect's array of microphones collects audio, which is processed and allows the device to perform voice recognition features.

Kinect uses software technology and on range camera technology that can interpret specific gestures, making completely hands-free control of electronic devices possible by using an infrared projector and camera and a special microchip to track the movement of objects and individuals in three dimensions. This 3D scanner system called Light Coding employs a variant of image-based 3D reconstruction.

The Kinect sensor is a horizontal bar connected to a small base with a motorized pivot and is designed to be positioned lengthwise above or below the video display. The device features an "RGB camera, depth sensor and multi-array microphone running proprietary software", which provide full-body 3D motion capture, facial recognition and voice recognition capabilities. Kinect sensor's microphone array enables Xbox 360 to conduct acoustic source localization and ambient noise suppression.

The depth sensor consists of an infrared laser projector combined with a monochrome CMOS sensor, which captures video data in 3D under any ambient light conditions. The sensing range of the depth sensor is adjustable, and Kinect software is capable of automatically calibrating the sensor based on gameplay and the player's physical environment, accommodating for the presence of furniture or other obstacles.

The software technology enables advanced gesture recognition, facial recognition and voice recognition. Kinect is capable of simultaneously tracking up to six people, including two active players for motion analysis with a feature extraction of 20 joints per player.

Kinect uses a laser grid to calculate depth. Kinect's various sensors output video at a frame rate of ~9 Hz to 30 Hz depending on resolution. The default RGB video stream uses 8-bit VGA resolution (640×480 pixels) with a Bayer color filter, but the hardware is capable of resolutions up to 1280×1024 (at a lower frame rate) and other color formats such as UYVY. The monochrome depth sensing video stream is in VGA resolution (640×480 pixels) with 11-bit depth, which provides 2,048 levels of sensitivity.

The Kinect can also stream the view from its IR camera directly (i.e.: before it has been converted into a depth map) as 640×480 video, or 1280×1024 at a lower frame rate.

The Kinect sensor has a practical ranging limit of 1.2-3.5 m (3.9-11.5 ft) distance when used with the Xbox software. The area required to use Kinect is roughly 6 m2, although the sensor can maintain tracking through an extended range of approximately 0.7-6 m (2.3-19.7 ft). The sensor has an angular field of view of 57° horizontally and 43° vertically, while the motorized pivot is capable of tilting the sensor up to 27° either up or down. The horizontal field of the Kinect sensor at the minimum viewing distance of ~0.8 m (2.6 ft) is therefore ~87 cm (34 in), and the vertical field is ~63 cm (25 in), resulting in a resolution of just over 1.3 mm (0.051 in) per pixel.

The microphone array features four microphone capsules and operates with each channel processing 16-bit audio at a sampling rate of 16 kHz. Currently the Kinect provides the voice commands (it has its own microphone array in it and voice command software is part of the API) although you could have a secondary voice command system.

Because the Kinect sensor's motorized tilt mechanism requires more power than the Xbox 360's USB ports can supply, the device makes use of a proprietary connector combining USB communication with additional power. Redesigned Xbox 360 S models include a special AUX port for accommodating the connector, while older models require a special power supply cable (included with the sensor) that splits the connection into separate USB and power connections; power is supplied from the mains by way of an AC adapter.

Leap Motion Controller

The LEAP motion device is a small USB connected sensor that senses hand movements in an area above where it located to provide hand free control of various computer tasks.

The Leap Motion controller is a small USB peripheral device, which is designed to be placed on a physical desktop, facing upward. Using two monochromatic IR cameras and three infrared LEDs, the device observes a roughly hemispherical area, to a distance of about 1 meter. The LEDs generate pattern-less IR light and the cameras generate almost 300 frames per second of reflected data, which is then sent through a USB cable to the host computer, where it is analyzed by the Leap Motion controller software using "complex maths" synthesizing 3D position data by comparing the 2D frames generated by the two cameras.

The smaller observation area and higher resolution of the device differentiates the product from the Kinect, which is more suitable for whole-body tracking in a space the size of a living room. The Leap can allow a user to perform tasks such as navigating a website, using pinch-to-zoom gestures on maps, high-precision drawing, and manipulating complex 3D data visualizations.

Video Display Software

In another embodiment, the term video is to be read to include any type of content that is displayed according to the traditional video format having a particular number of frames per second, and so forth.

Annotation Tool Software

The annotation tool is selected using a voice command or a touchless arm or hand movement to select from the control menu on the screen, aka a gesture command. Once the annotation tool is selected, the annotation tool may be controlled using gesture commands, voice command, or both. Annotations can include using gestures to draw freeform or from a selection of geometric shapes such as lines, arrows, circles, ellipses, squares, rectangles, triangles, as well as other polygonal shapes such as diamonds, stars, and the like. In another important aspect, there is provided a pointer for pointing to anatomy displayed on the video in a non-touch manner. The annotation tool may also include a zooming tool for creating a segment of the video feed that is displayed in a magnified or zoomed manner. A text box may also be included in the annotation tool and text may be inputted using voice to text capability, or using sign languages or specialized custom user-developed gestures.

The annotation process involves creating an annotation data structure apart from the indexed data structure of the video file. This annotation data structure includes an indication of the index of the annotated frame, a graphical element, which is displayed overlaying the annotated frame when it is displayed, and a data field storing the actual data of the annotation. The annotation data structure can be communicated independently of the video frame, does not alter the video frame, and can take on the format most effective for communicating the particular annotation desired.

A graphic annotation may be static (e.g., an illustration that does not change over the length that it is displayed) or dynamic. A static graphic may be a persistent annotation that remains in a given location within the user interface/display for a period of time. Such an annotation may or may not be locked onto an underlying feature identified within the video. A dynamic graphic illustration may comprise a set of one or more frames that are associated with a video segment of the video, a changing or moving annotation. When a dynamic graphic annotation is encountered, the set of one or more annotated frames may be displayed and overlaid over the frames of the video.

Example—System

A system for annotating endoscopic video display during an endoscopic surgical procedure is set up. The system comprises an endoscopy apparatus, one or more computing systems, one or more displays, and a gesture and voice command input device for annotating the video.

The endoscopy device has an endoscope with a rigid or flexible tube, a light source directed via a fiber optic system into the tube, an imaging component within the tube for transmitting image or video to a display screen, and one or more medical instruments within the tube for performing a medical procedure;

The computing systems include a computing system that is part of the endoscopy device. However, these computing systems are not capable of working with the Kinect API, which requires the video to be ported out thru DVI to a secondary computing system, such as a Microsoft laptop, which has all of the necessary drivers and compression software, which then ports out to the video displays.

The gesture and voice command system is a Kinect or Kinect-type system that is capable of detecting arm and hand gestures, and capable of receiving voice commands, from multiple parties, and translating these gestures and voice commands to annotation inputs to the secondary image layer that is generated by the second computer and is overlaid onto the endoscopic video.

The annotation tool is a menu driven tool that can provide for standard annotation features such as a pointer tool, a pen for drawing lines, geometric shapes, or free form lines, a snapshot tool for capturing still images and timed video segments, a zoom magnification tool, a tool for editing and/or resetting the annotation image. The annotation tool menu can also be configured to work with the endoscopy camera's native features, such as providing increased contrast, providing infrared illumination, and provide near-infrared visualization. The annotation tool can also be configured to control the fiberoptic light source to provide dynamic levels of illumination, and lighting enhancement/desaturation.

Example—Endoscopy Training

In one example, the invention provides a gestural image annotation system for resident surgeons performing a minimally invasive surgery to reference and annotate endoscopic views based on Kinect verbal and gestural commands.

In this example, an endoscopic video is piped out of the Stryker Corporation's Park Trainer®, available from Stryker Corp., 5900 Optical Court, San Jose, Calif. 95138 USA, (408) 754-2000, and is imported into the inventive system and displayed on the Park Trainer monitor. In one preferred aspect, the endoscopic video is sent wirelessly from the endoscopic camera eliminating the need for the DVI cable. When the user uses a combination of audio key words and hand movements to trigger different abilities of the system, the Kinect extracts and detects cues, determines a command for one or more cues, and recognizes which of a plurality of different possible commands to process.

In this example, the one or more cues can include one or more gesture commands, an input means in real time, and a processing means for representing a gestural image annotation system for resident surgeons performing a minimally invasive surgery to reference and annotate endoscopic views.

In another aspect, the gestural image annotation system outputs a real-time endoscopic video display of the simulation from the Stryker Corporation's Park Trainer® and is imported into the gestural image annotation system and then displayed on the Park Trainer monitor. Vector processing means are then used for representing the annotation in each image displayed of the simulation anatomy.

It is contemplated that voice control will also be used for gaining control and gestures for markings. This will provide a method for providing training situations that occur in minimally invasive surgery procedures in order to train surgical residents to perceive and appropriate digital representations of the body.

Example—Development of Coding Database

In this example, a minimum of ten (10) laparoscopic surgeries were observed, recorded and analyzed. All the videos are imported into the software to be reviewed, coded, and compared.

Figure 2:
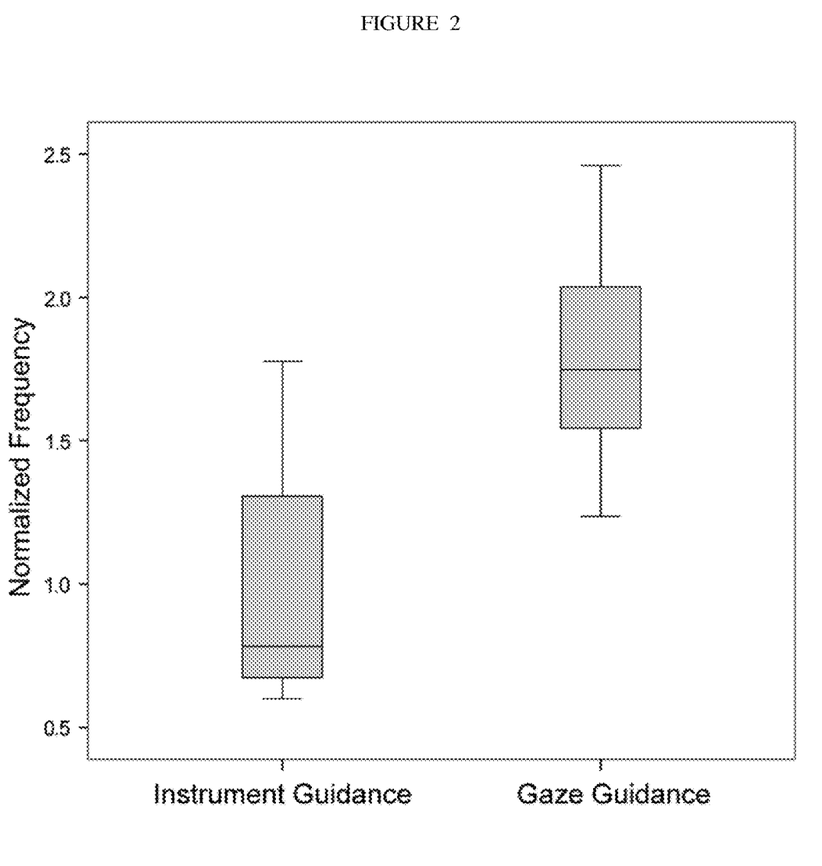
FIG. 2 is a bar graph showing the difference between gaze training and instrument training in laparoscopy.

Referring now to FIG. 2, of the total 1984 instructions given in the ten cases (10.95 h), the instructions in the Operating Room were categorized into two main classes instrument guidance (38.51%) and gaze guidance (61.49%). The results show that residents, who had gone through no gaze training, greatly depended on the attending surgeons' verbal guidance to look at the correct target. The results indicate that the OR-based training in laparoscopic surgery focuses more on gaze guidance instead of instrument instruction and implies that expert gaze strategy is the premise of the performance in surgical tasks and requires continuous attention of both the attending surgeons and residents.

| Instruction | Aim | Frequency |
| --- | --- | --- |
| Instrument guidance | Directions to the targets | 581 |
| | Instrument manipulation | 107 |
| | Instrument interaction | 76 |
| Gaze guidance | Target identification | 821 |
| | Gaze fixation | 399 |

Example—Coding of Deixis

In this example, a library of deictic endoscopic surgical commands are obtained and programmed into a gaze and instrument instruction software module.

Figure 3:
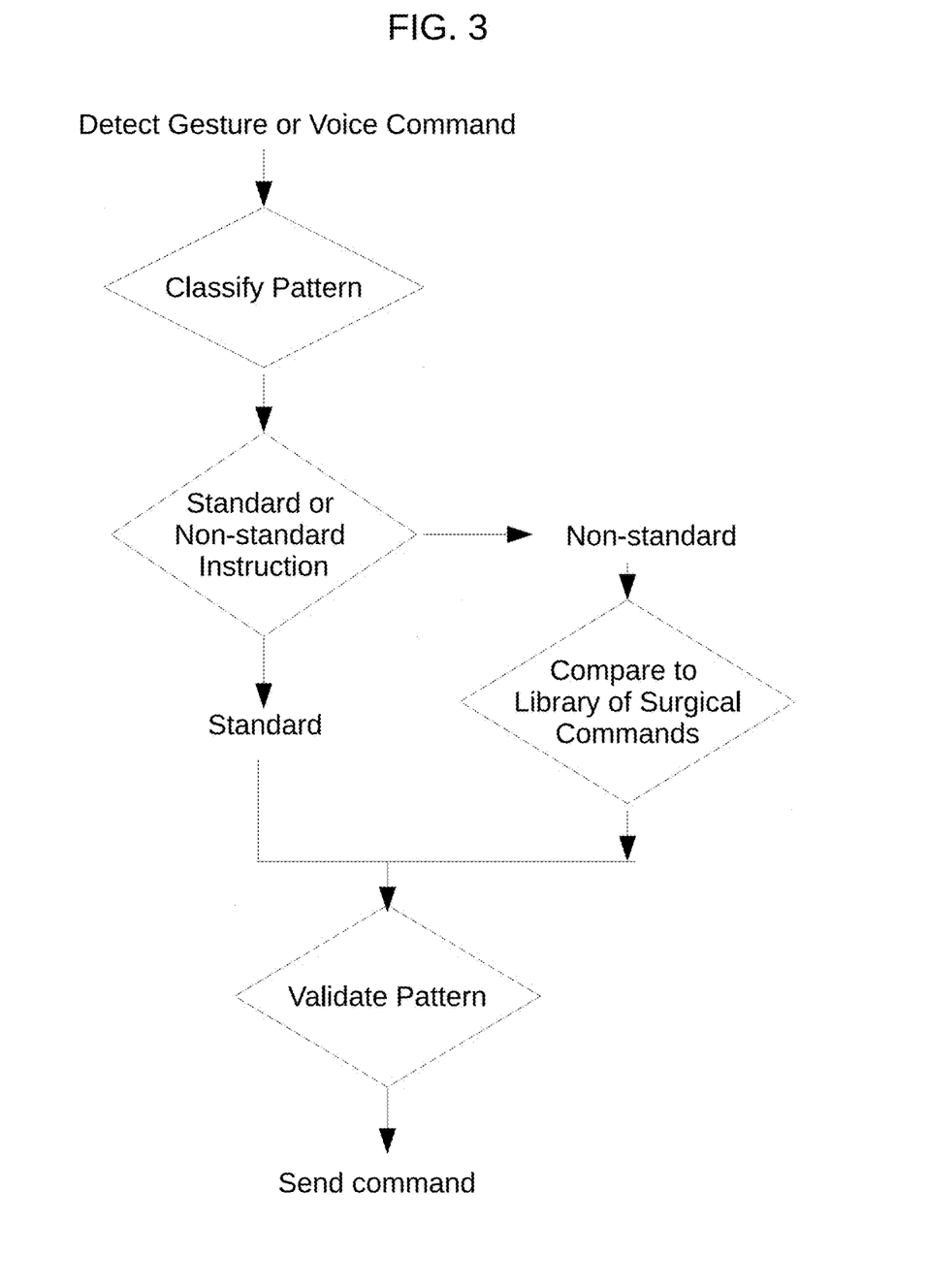
FIG. 3 is logic flow chart showing receipt of a verbal or gesture command with the optional use of a pre-programmed or trained surgical/deictic library.

FIG. 3 is a logic flowchart showing how a Kinect device would detect a gesture or voice command. Software would classify the pattern to to qualify the command and avoid unintentional activity. The qualified command could then optionally be sorted into standard annotation commands and non-standard, specialized commands. Specialized commands would then be forwarded to a library module for verification. Verified surgical commands commands would then be validated, and the command sent to the annotation tool. Standard commands would be directly forwarded for validation without library screening.

Figure 4:
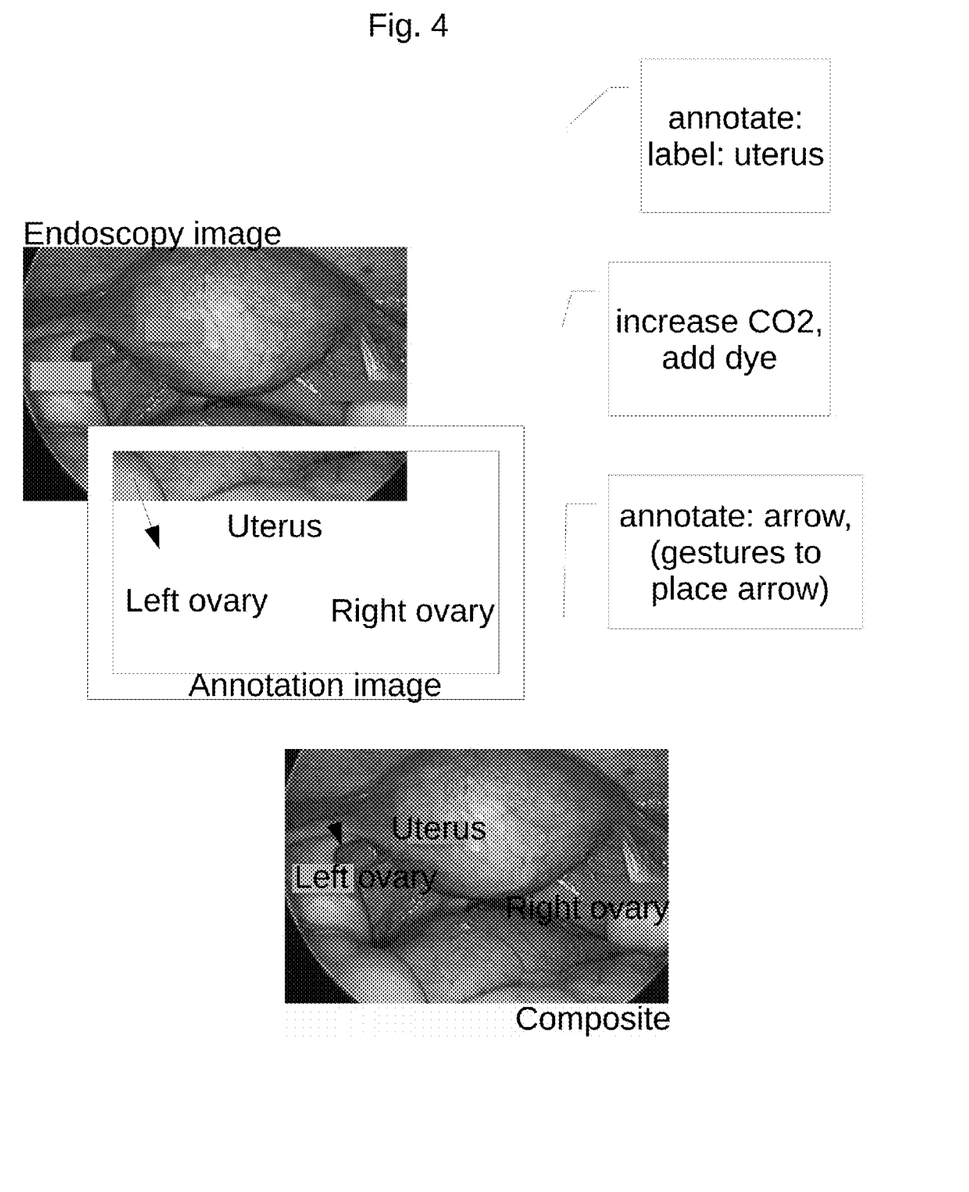
FIG. 4 is a graphic showing an endoscopy image, an annotation image, and a composite image.

Referring now to FIG. 4, FIG. 4 shows a sample endoscopy image with an annotation image overlay. The composite of both images is shown at the bottom of FIG. 4. Sample dialogue and gestures from the Operating Room are shown on the right hand side of FIG. 4. The first dialogue box contains a verbal annotation command to add a label, and to associate the text "uterus" to the newly generated label. The next dialogue box shows an example of surgical dialogue which would not trigger an annotation. The library module could be configured with white list exceptions to the annotation commands. The third dialogue box shows a verbal annotation command to add an arrow, which could the be placed using a aseptic/sterile non-touch hand gesture from the practitioner.

Example—Organ Transplant Assessment

In this example, the present invention is used over a long distance network in a telemedicine approach to improve assessment of transplant organs for transplant organ recovery surgery. The scarcity of donor organs and the need to ensure that all implanted organs will provide quality, long-term function for their recipients mandates very careful organ selection. Often, organ recovery occurs far from the hospital of the transplant recipient. In order to save time, the recovery team travels to the donor and assesses the organs for viability while the transplant team will begin to prepare the patient. Currently, a remote recovery surgeon discusses any concerns regarding donor organ assessment with the implant surgeon by phone prior to proceeding with removal or to terminating the recovery. There is a need to conduct these assessments thoroughly yet quickly and then be able to effectively transmit the crucial pieces of information back to the implant surgeon for final recovery decision-making.

In order to enhance information sharing and decision-making, and improve assessment in a limited window of time, transplant surgeons utilize the inventive video-enabled telecommunication devices in their discussions. The video, coupled with the consultation with an implanting surgeon at the time of procurement, permits improved sharing of organ function assessment and facilitates decision-making between recovery and implant surgeons.

Example—Collaborative Telemedicine

Figure 1:
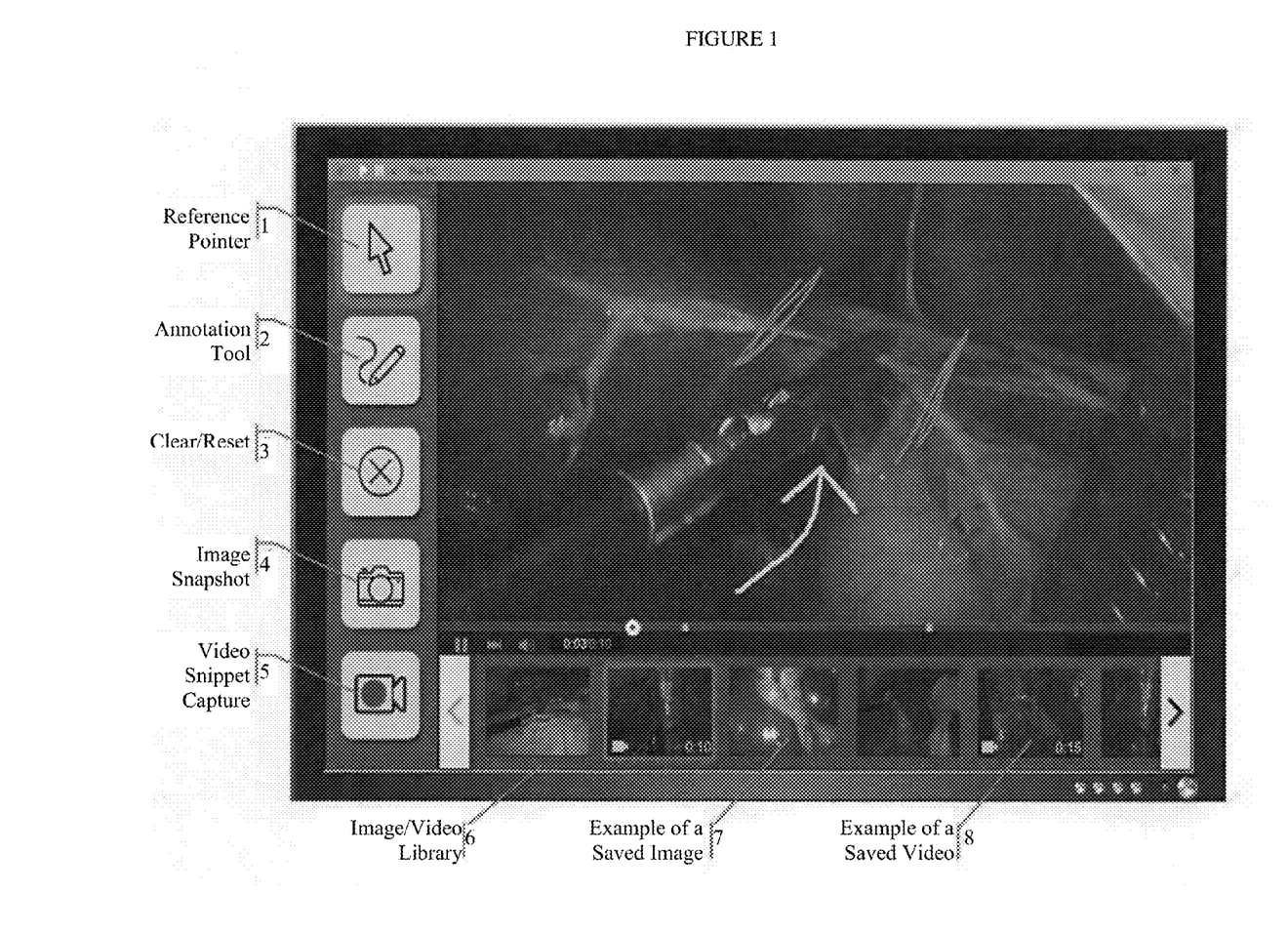
FIG. 1 is a marked-up photographic representation of a collaborative image interaction user interface.

FIG. 1 shows the user interface for both the helper and worker. The menu on the left side provides buttons that map to each of the available tools for live or saved images/videos:

(1) a reference pointer tool that displays a large pointer (currently active), (2) an annotation tool for drawing (example annotations are displayed on the image in the main window in the form of lines and arrows), (3) a clear/reset button to clear annotations or reset the view back to the live video, (4) an image snapshot button to save still images from the live video to the Image/Video Library, and (5) a video snippet capture button to start/stop recording from the live video to the Image/Video Library.

(6) Image/Video Library at the bottom of the screen displays the (7) image snapshots that have been taken or the (8) video snippets that have been saved.

Selecting one of these items displays it in the main window (the second item, a video of 10 seconds is currently selected and playing).

If no image or video is selected, then the video being displayed in the main window is the live feed from the input device.

The reference pointer and image annotation tool will overlay on all images or video—i.e. live feed or saved images or videos.

At any given time, either surgeon can use the referencing, annotation, or video capture/playback tools and, most importantly, they can use the same tool at the same time. For instance, the two different colors of annotations are indicative of the two different collaborator's annotations. In addition, the reference pointer is also color-coded so two reference pointers can be displayed at the same time.

As the worker will be a surgeon who must remain sterile, voice control will be used for turning on and off the system's gesture recognition detection as well as giving discrete commands such as "clear" to clear the annotations on the screen. Gestures will be used for telestration—much like on an instant replay video clip during a football game—and other mouse replacement movements. The remote surgeon will have a tablet computer that is running the application and can use a mouse, stylus, or finger to interact with the application.

For secure video and annotation transmission, the invention may leverage the VSee API. VSee provides the video compression, transmission, and server storage. VSee's API is preferable to OpenTok, that would require us to set up our own server, or Skype, that has discontinued support for the desktop API. VSee is built on the XMPP video standard that is, for instance, used by Google Talk and Facebook chat.

Example—Tele-Illustration Aka "Telestration

An expert or mentor surgeon may telestrate by connecting as one of the annotative users of the present system. Using a local connection to an annotation tool that is networked to the inventive system's display, the mentor surgeon can interact with the display screen to generate a telestration graphic input which is provided via the remote user interface to a telestration graphic transmit unit. The telestration graphic transmit unit then transmits over TCP/IP, automatically in real-time or upon user command, the telestration graphic input as metadata, which may be in a selected graphics language format, to the telestration graphic receive unit in the surgeon's computer. Contrary to the very high data transfer rates and the sensitivity to network latency that is observed in remote and local control of robotic endoscopy, the advantage of tele-illustration is that video and audio instruction can be compressed using traditional compression algorithms. Thus, the requirements for very high data transfer rates and low network latency are avoided.

In a preferred aspect, the invention uses VSee, which is a proprietary low-bandwidth, group video chat and screen-sharing software tool. VSee uses a managed peer-to-peer architecture, and although a server is used for admin and address lookup, the data does not pass through the server. VSee uses a network-sensing algorithm that adapts to network conditions allowing it to deliver video over very low-bandwidth connections, e.g. 3G. The VSee service allows multiple users in various locations to communicate in real-time by video and audio. Its interface is able to concurrently display video faces and allow users annotate on shared screen content. VSee sends video at rates as low as 50 kbit/s and is capable of real-time video communication over 3G cellular networks.

Having described embodiments for a system and method for real-time annotations of endoscopic video, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A system for annotating real-time endoscopic video display during an endoscopic surgical procedure, comprising:

a gaze and instrument instructions software module having programmed therein a library of deictic endoscopic surgical commands comprising instrument guidance commands and gaze guidance commands, said instrument guidance commands comprising a direction to target annotation, an instrument manipulation, and an instrument interaction, and said gaze guidance commands comprising a target identification annotation and a gaze fixation annotation;

a gesture or voice command software module in communication with the gaze and instrument instructions software module, wherein the gaze and instrument instructions software module includes programming instructions to execute a gesture or voice command process, a command qualifier process, a standard or specialized command process, a specialized command verification process, and a command validation process;

a library module for verification of specialized commands is associated with the gaze and instrument instructions software module;

an endoscopy apparatus, the endoscopy apparatus comprising an endoscope, the endoscope comprising a rigid or flexible tube, a light source directed via a fiber optic system into the tube, an endoscopic video imaging component disposed within the tube for transmitting image or video to a display screen, and one or more medical instruments disposed within the tube for performing a medical procedure;

a computing system in operative association with the endoscopy apparatus, wherein the computer system is configured to receive, store, and process the transmitted image or video;

one or more displays connected to the computing system, the one or more displays configured to receive and display the transmitted image or video;

a gesture and voice command input device connected to the computing system, the gesture and voice command input device associated with the gaze and instrument instructions software module, wherein audio key words and hand movements trigger a process to extract and detect one or more cues, associate a command with each of said one or more cues, and process the command with the gaze and instrument instructions software module; and, an annotation tool for annotating the image or video, the annotation tool comprising program instructions stored on non-transitory computer-readable storage media that upon execution by a processor associated with the computing system receives input from the gesture and voice command input device and outputs one or more annotations to the one or more displays, wherein said one or more annotations overlays the endoscopy video and said one or more annotations comprises a text label, a reference pointer, an arrow, a line, one or more tool buttons including a reference pointer tool button, an annotation tool button, a clear/reset button, an image snapshot button, a video snippet capture button, an image/video library button, a saved image button, and a saved video button.

2. The system of claim 1, wherein the computing system comprises a first computer and a second computer, the first computer is part of the endoscopy apparatus and outputs an endoscopy video, the second computer is operatively associated with the annotation tool and receives the endoscopy video output of the first computer, the second computer outputs a first user interface and a second user interface to a display, the first user interface provides a view of video from the endoscopy apparatus, the second user interface associated with annotating the video, the second user interface overlaying the first user interface, wherein in response to a voice command or gesture command input to the second computer, the annotation tool outputs an annotation to the second user interface, the annotation comprising a user image and a video position tag.

3. The system of claim 1, wherein the video is live video displayed concurrent with the output from the endoscopic camera, and the annotation is a persistent annotation.

4. The system of claim 1, wherein the system further comprises a second gesture command input device and a second voice command input device, capable of operation by a second person.

5. The system of claim 4, wherein the second gesture command input device and the second voice command input device, capable of operation by a second person, are remote from the first gesture command input device and the first voice command input device, and not at the same location, wherein the locations are connected with a 50 kbit/s bandwidth screen-sharing tool.

6. The system of claim 1, wherein the system further comprises a second annotation tool.

7. The system of claim 6, wherein the first and second annotation tools annotate in different colors.

8. The system of claim 7, wherein the first and second annotation tools are remote from each other and are not operated at the same location, and the output from the first and second annotation tools are each separately displayed to the same second user interface.

9. A graphical user interface, comprising: (i) a display portion that receives video output from the system of claim 1; (ii) a display portion that provides a link to an image/video library; and (iii) a display portion that provides one or more control button links to a video annotation tool.

10. The graphical user interface of claim 9, wherein the one or more button links further comprises a reference pointer, a reset, and an image or video capture.

11. A method for annotating endoscopic video display during an endoscopic surgical procedure implemented at least in part by a computer, the method comprising the steps: using the system of claim 1, displaying a first user interface capable of providing a view of video from an endoscopic camera; displaying a second user interface associated with annotating the video, the second user interface overlaying the first user interface; receiving a voice command or gesture command to select an annotation tool associated with the second user interlace; receiving an annotation to the video from the annotation tool, the annotation comprising a user image and a video time tag; displaying the annotation associated with the second user interlace overlaid over the first user interface.

12. The method of claim 11, wherein the annotation comprises one or more graphical annotations.

13. The method of claim 11, wherein the video is stored with the annotation.

14. The method of claim 11, wherein the video is live video displayed concurrent with the output from the endoscopic camera, and the annotation is a persistent annotation.

15. The method of claim 11, wherein the step of receiving a voice command or gesture command is performed by two or more persons.

16. The method of claim wherein the two or more persons are remote from each other and not at the same location.

17. The method of claim 11, wherein the step of receiving an annotation is performed by two or more annotation tools.

18. The method of claim 17, wherein the two or more annotation tools annotate in different colors.

19. The method of claim 18, wherein the two or more annotation tools are remote from each other and are not operated at the same location, and the output from the two or more annotation tools are each separately displayed to the same second user interface.

* * * * *